United States Patent [19]

Nunn

[11] Patent Number: 5,164,096
[45] Date of Patent: Nov. 17, 1992

[54] BIOCIDE MICROENCAPSULATION

[75] Inventor: Maureen B. Nunn, Naperville, Ill.

[73] Assignee: Nalco Chemical Company, Naperville, Ill.

[21] Appl. No.: 786,626

[22] Filed: Nov. 1, 1991

[51] Int. Cl.$^5$ .............................. C02F 1/50
[52] U.S. Cl. ........................ 210/754; 210/764; 210/928; 252/176; 252/180; 422/37; 424/408; 424/419; 424/456; 428/402.2; 428/402.24; 514/963; 162/29
[58] Field of Search .......... 210/764, 928, 765, 754, 210/167; 428/402.2, 402.24; 424/408, 456, 419; 422/37; 252/176, 180; 514/963; 162/29

[56] References Cited

U.S. PATENT DOCUMENTS

| | | |
|---|---|---|
| 4,089,800 | 5/1978 | Temple .................................. 264/5 |
| 4,107,292 | 8/1978 | Nemeth ............................. 424/419 |
| 4,253,877 | 3/1981 | Miale et al. ...................... 428/402.2 |
| 4,277,364 | 7/1981 | Shasha et al. ..................... 424/419 |
| 4,285,765 | 8/1981 | Pera et al. ........................ 210/764 |
| 4,436,719 | 3/1984 | Lindaberry ....................... 424/419 |
| 4,447,411 | 5/1984 | Langdon .......................... 424/419 |
| 4,561,981 | 12/1985 | Characklis ....................... 210/698 |
| 4,808,408 | 2/1989 | Baker et al. ..................... 424/419 |

*Primary Examiner*—Stanley S. Silverman
*Assistant Examiner*—Neil M. McCarthy
*Attorney, Agent, or Firm*—Robert A. Miller; James J. Drake

[57] ABSTRACT

Biocide treatment of the water system of a papermaking process comprising the steps of encapsulating the biocide as the core of the capsule in a water suspension, in which the shell is degradable at high water dilution, and introducing the microcapsules into the water stream to undergo dilution release.

6 Claims, 2 Drawing Sheets

BIOCIDE MICROENCAPSULATION

INTRODUCTION

This invention relates to biocide treatment of industrial water systems, particularly water systems involved in a papermaking process.

BACKGROUND

It is customary in many industrial water systems, particularly papermaking to add a biocide to the water phase to destroy bacteria which have a detrimental effect on the water quality or the quality of products in contact with these waters, such as the paper products. The biocide is usually pumped or added to the waters as a solution of an active biocide. The biocides usually have a terrible odor and some toxic hazard is involved, such as skin sensitivity, if nothing else. After all, most biocides are lethal in appropriate dosages, to the bacteria contained in these industrial waters. The safety regulations can be costly to administer. The object of the present invention is to solve these handling and exposure problems by inoculating the water system with a biocide insulated by microencapsulation. The capsulating film is then either broken by mechanical energy, such as encountered in pumps and mixers, or hydrolyzed in contact with the industrial waters, thereby releasing the biocide into the contaminated waters.

BRIEF SUMMARY OF THE INVENTION

Under and in accordance with the present invention a dispersion of biocide microcapsules is prepared. The biocide is contained within the core or internal phase of the microcapsules. The continuous outer shell or outer film is an innocuous non-toxic, nonsensitizing gum gelatin membrane. These microcapsules are easily added to water systems to inoculate the water system and once diluted by the water system the membrane is dissolved, hydrolyzed, or ruptured by the means for pumping and/or mixing and by the dilution water to release the biocide actives constituting the core of the capsule.

The biocidal odor is thus masked, and by the same token the biocidal toxicity/sensitizing is controlled and the encapsulated biocide is in a state of harmless isolation until released and added to the industrial waters and dilution occurs.

GENERAL DESCRIPTION

Figure 1:
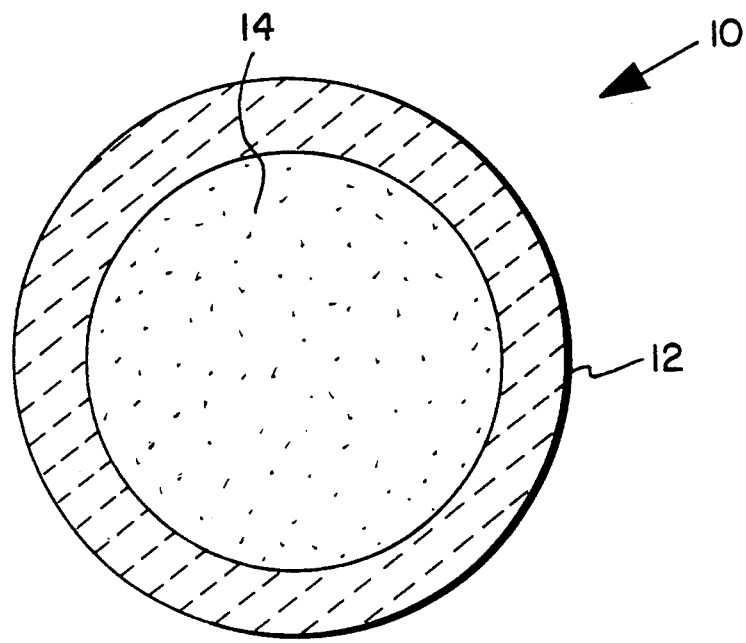
FIG. 1 is a diagram of a typical microcapsule featured in the present invention.
Figure 1A:
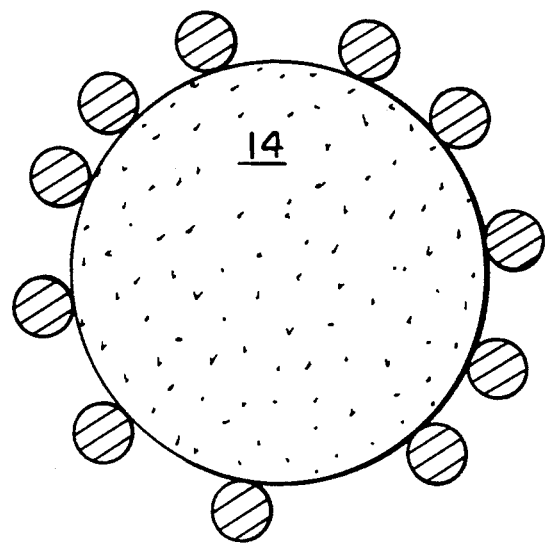
FIG. 1A is a diagram similar to FIG. 1 but showing the embryo or coacervation state.
Figure 2:
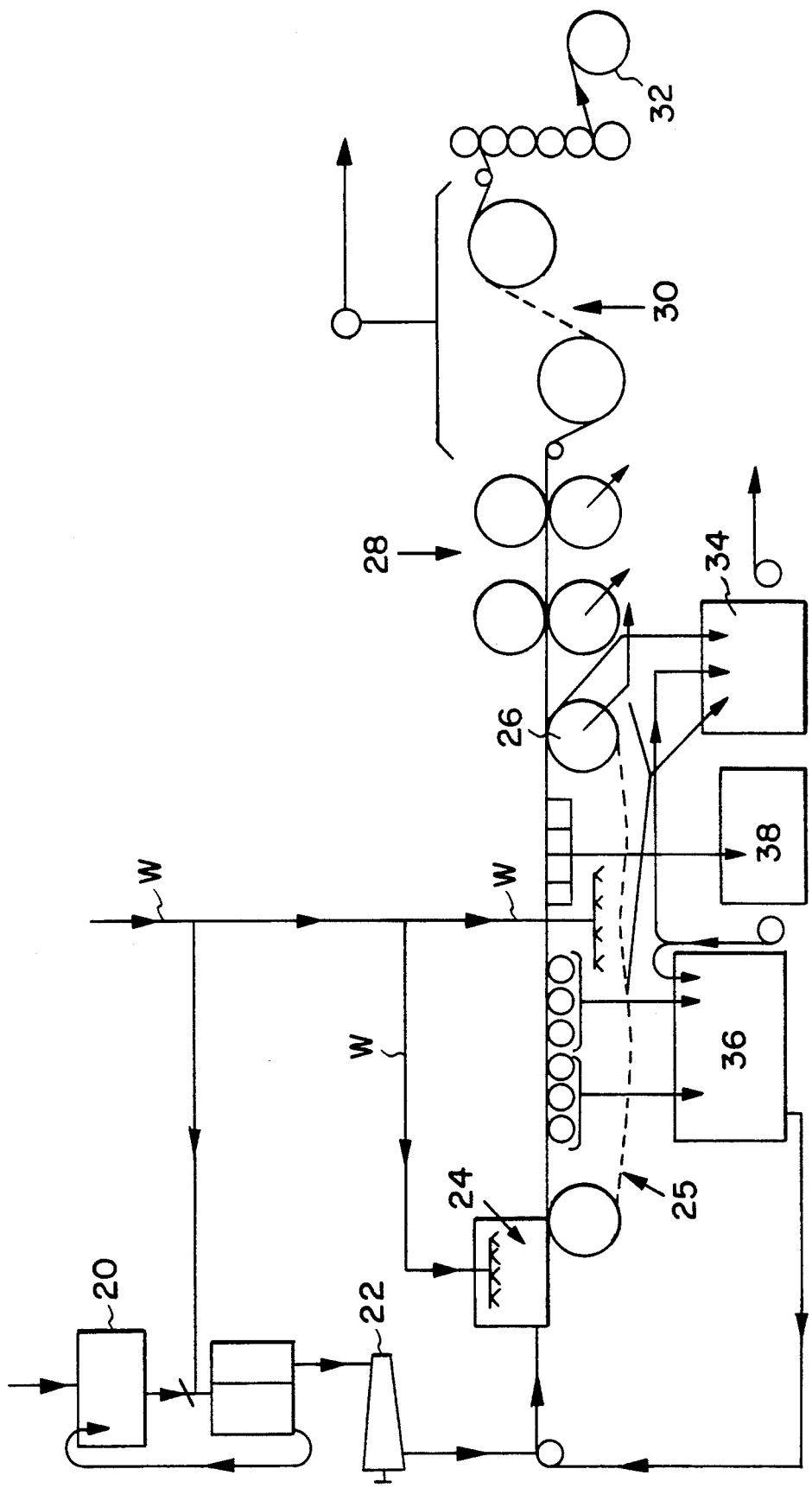
FIG. 2 is a diagram of a typical papermaking process in which the present invention may be employed.

Microcapsules 10, FIG. 1, have an outer continuous shell or wall 12 of a material which will degrade in the presence of a large volume of water represented by the industrial water systems. Representative of their water system are recirculating cooling waters, swimming pools, and industrial baths and holding tanks, and finally industrial pulping and papermaking process, such as represented in FIG. 2. The core or internal phase 14 is a biocide, either pure, or "neat", or in solution.

The microcapsules are preferably produced in a water suspension and in a concentration that does not degrade the protective shell or film as the result of aqueous dilution. The manufacture is thus subcritical regarding the rupture of the protective encapsulating film or shell. This encapsulated biocide suspension can be contained in drums or other containers, which are the pulp & paper processing plant, the oil refinery, the industrial power generating plant or the processing mill. The biocide encapsulate suspension can be pumped into the industrial water system, such as papermaking process, typified by a Foudrinier paper machine diagrammed in FIG. 2. The consequent shearing energy and dilution in the industrial water system, including a paper process stream, is so enormous that the encapsulative shell dissolves, releasing the biocide.

DETAILED DESCRIPTION

Neither the core biocide material nor in some cases the substances of the wall encapsulating shell or is new. Preferably the core biocide is bistrichloromethylsulfone. The encapsulating wall or shell may, for example, a mixture of gum arabic and gelatin.

However, any biocides may be used, preferably water. Soluble biocides (or water dispersable biocides, perhaps formulating with common cosolvents or dispersing agents, such as ethylene glycols, hexylene glycol or surfactants, detergents, or the like). Also, the encapsulation film, shell and/or wall material may be other than those mentioned above.

EXAMPLE 1

A. 1:8 (weight) gum arabic dissolved in water; 20 grams of gum arabic; 160 grams water.

B. 1.8 (weight) gelatin dissolved in water; 20 grams (pork skin) gelatin (bloom strength 300), 160 grams water.

Take 18 grams of A and eight grams of the biocide which 34.3 percent by weight bistrichloromethylsulfone (actives) dissolved in hexylene glycol. This mixture is homogenized and then funneled to and stirred at room temperature (650 rpm) in a vessel equipped with a stir tester (Heller), forming an emulsion or dispersion of gum arabic and the biocide in water. The water is the external phase. To this emulsion is added 18 grams of B and the contents of the vessel are heated for about one hour at 50° C., causing the gum arabic and gelatin to react, thereby forming an encapsulating wall, film, or shell. After this time lapse, 160 ml. of distilled water is added drop-wise to the vessel. During this stage, the gum arabic-gelatin combination coacervates, or congeals, forming tiny, discrete particles about the biocide core and eventually coalescing to form the continuous shell 12, as represented in FIG. 1.

The reactor contents are then cooled to 0° C. and monitored at this low temperature while stirring, again at about 650 rpm using the Heller ® Stir Tester, until microscopy inspection reveals that the gum-gleatin coacervate particles have indeed coalesced to complete a shell or continuum wall about the biocide cores.

Heller ® is a registered trademark.

The capsules in this experiment are about 50 microns diameter, and are stably dispersed or suspended in water. However, the biocide capsules may range in diameter from about 20 microns up to about 500 to 1,000 microns depending upon the biocide, its concentration, the encapsulation agent(s), their concentration, the reaction time, the energy and time of mixing, and other such variables. The encapsulating film is formed by complex coacervation of the mentioned reactants, which film is ruptured merely by dilution.

The suspended state prevails when diluted with distilled water 1:10. The microcapsules are still intact at 1:100 dilution. These concentrations may be viewed as sub-critical, that is, water dilution is less than the critical amount to degrade the shell. However, at 1:1000 dilution the microcapsule disappears because of dilution release, that is, extreme dilution in a water system destroys ruptures, or breaks the capsule shell. Similar results may be observed at high energy shear levels, below the 1:1000 dilution.

The invention is practiced in the industrial water system. For example, in a papermaking process, see FIG. 2, which diagrams a Foudrinier paper making process, it is sufficient to identify (proceeding downstream) the machine chest 20, Jordan refiner 22, headbox 24, the forming wire 25, couch 26, presses 28, the driers 30 and reel 32.

The flow of clarified water is identified by reference character W. Industrial water is recirculated from the save-all 34, the silo 36 and the Broughton tank 38.

In particular, FIG. 2, the biocide capsules of Example 1 may be dispersed in water at a low concentration, e.g. from 1:10 to 1:100, and these biocide formulations can be transmitted to the plant in drums or other containers without apprehension of toxic reaction, sensitizing reaction or of loss of integrity. At the plant, the encapsulated biocide suspension is pumped into the water system at virtually any convenient point upstream of contamination, for example, in the papermaking process, any point upstreams of the couch 26. There is an enormous dilution because the industrial water system in a typical process may be circulating up to 100–10,000 gallons per hour, or more. A typical pumping rate for the microcapsule biocide product would be about 0.010 gallons per hour to about 120 gallons per hour. This could provide about capsule parts 10–100,000 active capsules (30–95% biocide)—per million parts of water volume.

Endless and unnecessary experimentation would be required to determine the absolute volume of water for dilution release. Indeed, this emphasizes one advantage of the present invention, that the water system, such as the paper system of FIG. 2, is of such enormous volume that dilution release is essentially absolute. The enormous amount of water employed in these industrial systems, i.e. the papermaking system, is far more than the 1:1000 dilution whereat degradation or dilution release does occur.

Other biocides may, of course be used, traditional in such industrial water systems as power plant cooling systems, refinery or chemical processing cooling systems, or industrial processing waters, such as breweries, and the pulp and papermaking industry, and encapsulating shells other than that of example may be employed as long as the shell safeguards the core until ruptured by high energy shear or dilution release.

Hence, while the preferred embodiment of core and shell is set forth, it is to be understood that other biocides may be employed along with other, equivalent, shell substances.

What is claimed is:

1. A method of inoculating industrial water systems with a biocide comprising the step of introducing into the water system a stable dispersion of microcapsules in water, said microcapsules comprising an internal core containing the biocide and a continuous outer wall comprising a water soluble composition as to be dissolved by sufficient dilution of said dispersion in the system water, thereby releasing the biocide into the system water, said dispersion comprising said microcapsules in a concentration which provides less than a critical amount of water needed to dissolve the microcapsules in said dispersion.

2. The method according to claim 1 wherein the biocide is bistrichloromethylsulfone and the shell is a gum arabic-gelatin combinate.

3. The method of claim 1 or 2 wherein the industrial water system is from a pulp and paper processing mill.

4. The method of claim 1 or 2 wherein the industrial water system is an open recirculating cooling water system.

5. The method of claim 1 or 2 wherein the biocide is an effective biocide for clams, mussels, and oysters, and the water system is a once-through cooling system for a power generation plant.

6. The method of claim 1 or 2 wherein the biocide is dispersed in microcapsules containing core and a shell, said core containing at lest 25 volume % of biocide and said shell is a gum arabic—gelatin coacervate; said microcapsules being dispersed in water at a concentration of at least 20 weight percent, based on total formulation weight.

* * * * *